(12) United States Patent
Barrientos et al.

(10) Patent No.: US 12,708,547 B2
(45) Date of Patent: Aug. 18, 2026

(54) POSITIONING WEDGE

(71) Applicant: OSSUR ICELAND EHF, Reykjavik (IS)

(72) Inventors: Matthew Barrientos, Foothill Ranch, CA (US); Mark Harman Powell, Foothill Ranch, CA (US); Asdis Bjornsson, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 19/001,786

(22) Filed: Dec. 26, 2024

(65) Prior Publication Data

US 2025/0120845 A1 Apr. 17, 2025

Related U.S. Application Data

(63) Continuation of application No. 17/766,639, filed as application No. PCT/US2020/056794 on Oct. 22, 2020, now Pat. No. 12,213,903.

(60) Provisional application No. 62/925,061, filed on Oct. 23, 2019.

(51) Int. Cl.
*A61F 5/37* (2006.01)

(52) U.S. Cl.
CPC .................................. *A61F 5/3753* (2013.01)

(58) Field of Classification Search
CPC ... A61F 5/3746; A61F 5/3753; A61G 7/0755; A61G 7/075; A47G 9/1009; A47G 9/1027; A47G 9/1036; A47G 9/1045; A47G 9/1054; A47G 9/1063; A47G 7/1072; A47G 9/1081; A47G 9/109; A47G 9/10

See application file for complete search history.

(56) References Cited

U.S. PATENT DOCUMENTS

| | | | |
|---|---|---|---|
| 114,615 | A | 5/1871 | Smitley |
| 3,780,729 | A | 12/1973 | Garnett |
| 4,487,199 | A | 12/1984 | Saringer |
| 4,497,316 | A | 2/1985 | Lilla |

(Continued)

FOREIGN PATENT DOCUMENTS

| | | |
|---|---|---|
| DE | 20116743 U | 1/2002 |
| EP | 1013248 A1 | 6/2000 |

(Continued)

OTHER PUBLICATIONS

International Search Report and Written Opinion from PCT Application No. PCT/US2020/056794, mailed Feb. 2, 2021.

*Primary Examiner* — Camtu T Nguyen
(74) *Attorney, Agent, or Firm* — Workman Nydegger

(57) ABSTRACT

A positioning wedge is arranged as an interface between two anatomical portions of a human body to arrange the anatomical two portions at a predetermined angle or position relative to one another. The positioning wedge includes a main body having first and second sides connected to another by a bridge portion such that the first and second sides each define a predetermined angular profile. An insert can be arranged between the first and second sides to position the first and second sides relative to one another at a predetermined angle associated with the shape of the insert combined with the first and second sides. The insert is separable from, and attachable to the main body and the bridge portion extends over an end portion of the insert.

17 Claims, 9 Drawing Sheets

(56) References Cited

U.S. PATENT DOCUMENTS 4,598,701 A * 7/1986 Schaefer ............... A61F 5/3753 602/19
4,598,702 A 7/1986 Lilla
4,836,195 A 6/1989 Berrehail
5,385,536 A 1/1995 Burkhead et al.
5,407,420 A 4/1995 Bastyr et al.
5,418,991 A * 5/1995 Shiflett ..................... A61F 5/01 5/648
5,423,333 A 6/1995 Jensen et al.
5,665,058 A 9/1997 Young
5,746,218 A * 5/1998 Edge .................... A47C 20/021 128/DIG. 20
6,640,368 B2 * 11/2003 Roston ................. A47C 20/021 5/655.9
6,862,870 B1 3/2005 Coons
7,563,236 B2 7/2009 Kazmierczak et al.
8,016,780 B1 9/2011 Sickles
8,109,273 B2 2/2012 Golden et al.
8,273,041 B2 9/2012 Goumas
8,454,544 B2 6/2013 Barnes et al.
9,492,303 B2 11/2016 Golden et al.
9,545,155 B2 1/2017 James
9,700,453 B2 7/2017 Benenati
9,827,133 B1 11/2017 Krenzel
9,968,477 B2 5/2018 Lo
10,143,270 B2 12/2018 Fiedler et al.
10,231,862 B2 3/2019 Summit et al.
10,285,841 B2 5/2019 Pappady
10,736,767 B2 8/2020 Boileau et al.
10,758,442 B2 * 9/2020 Panigada ............... A61G 7/072
11,871,854 B2 1/2024 Barbalinardo et al.
12,213,903 B2 * 2/2025 Barrientos ............ A61F 5/3753
2009/0192424 A1 7/2009 Choudhury et al.
2010/0152635 A1 6/2010 Borden
2011/0046529 A1 * 2/2011 Vollbrecht ............ A61F 5/3753 602/20
2012/0101421 A1 4/2012 Albrecht
2012/0245498 A1 9/2012 Krenzel
2013/0074269 A1 3/2013 Phillips, II
2013/0317401 A1 11/2013 Joslin
2014/0194798 A1 7/2014 Sotereanos et al.
2014/0221888 A1 8/2014 Benenati
2014/0371644 A1 12/2014 Erbe et al.
2015/0135486 A1 5/2015 Fiedler et al.
2016/0256311 A1 9/2016 Lemmon et al.
2017/0042721 A1 2/2017 Golden et al.
2017/0165138 A1 * 6/2017 Mc Coy ............... A47C 20/021
2020/0253776 A1 8/2020 Boileau et al.
2023/0389719 A1 * 12/2023 Barbalinardo ........... A47G 9/10

FOREIGN PATENT DOCUMENTS

EP 2833754 B1 4/2016
EP 3108859 A1 12/2016
ES 2734679 T3 12/2019
JP 2005245611 A 9/2005
JP 6376930 B2 8/2018
WO 03071994 A2 2/2003
WO 2019020960 A1 1/2019

* cited by examiner 102
20
104
100
116
118
10
106
A 203
219
220
202
200
217
204
206
218
216
209
211
208
213
212
215
214
210

253
272
273
252
250
278
258
280
15
276
254
282
284
30
260
262
264
45
256
208
274
270
271
266
275

POSITIONING WEDGE

FIELD OF THE DISCLOSURE

The disclosure relates to a positioning wedge that may be an abduction pillow for post-surgical operations to position a limb relative to another body portion among at least one of a plurality of angles relative to one another.

BACKGROUND

After shoulder surgery, a shoulder is often placed in an immobilizer or sling for bracing and immobilization. The immobilizer is used to limit the motion of the shoulder so the recovering shoulder can heal. The immobilizer is often prescribed for a recovery period of four to six weeks after surgery, so there should be no reaching, lifting, pushing, or pulling the recovering shoulder during this recovery period. During recovery, the individual may remove their arm of the recovering shoulder from the sling to bend and straighten their elbow to perform elbow range-of-motion procedures, bathing, and dressing, for example.

Some clinicians use abduction pillows or a positioning wedge to unload and protect the shoulder repair combined with a shoulder immobilizer. The pillow is often made from soft but firm foam and an inflatable device that prevents at least one limb from "abducting" or moving away from the body's medial plane. The pillow can prevent the worsening of an injury or facilitate recovery from surgery by avoiding movement that could harm the healing tissue or by unloading the recovering surgical site and associated repair.

Studies have shown that abduction of the glenohumeral joint at a predetermined angle, such as an arm in extension relative to a body using an abduction pillow, can reduce tension on the supraspinatus anteriorly and posteriorly compared to placing a shoulder in position without an abduction pillow. Generally, a relatively larger angle can yet further reduce tension both anteriorly and posteriorly. For example, it has been found that using an abduction pillow during postoperative immobilization following arthroscopic rotator cuff repair may have a significant beneficial effect on an early postoperative range of motion.

While a larger angle abduction pillow may be used initially post-surgery, some protocols may comprise a step-down approach in the size of the pillow's angle unloads the shoulder. For example, the protocol may call for reduced angles in predetermined increments as the shoulder heals and the user undergoes rehabilitation.

Positioning wedges are not limited to the shoulder but may find uses in other applications. For example, a hip abduction pillow may maintain a user's legs in abduction following hip surgery. Straps may be used combined with the hip abduction pillow to keep the pillow between a user's legs with minimal migration.

Known positioning wedges are typically more effective in maintaining a body part relative to another than a conventional pillow. Known positioning wedges are often of a fixed size, and the sides are arranged in a set angular relationship, preventing a step-up or step-down of angles. While many wedges are formed from foam or similar material, other wedges are inflatable to different angles by which the limb is propped relative to another body portion. These inflatable wedges may lack the same firmness of the foam or similar material wedges and may not provide successful immobilization.

Some known positioning wedges may comprise merely a block of foam or similar forms that lacks flexibility or general accuracy for adaptation to a plurality of angles. A clinician may not have the means to adjust the block to a specified angle. An immobilizing device, such as a shoulder immobilizer or sling, may not cooperate effectively with the block. The clinician requires a positioning wedge that is not complicated or confusing for fitting and modification for a user recovering from an injury or surgery, particularly to the operating environment and the nature of the impaired user.

Along with its inability to adapt to a specific shoulder immobilizer, the foam block may not comfortably position the limb against or relative to another body portion. While a block of foam may seem simple, it may lack repeatable donning as the user doffs and dons the immobilizer and does not consistently position the block in an intended manner.

There is a need for a positioning wedge that is easier to use over current solutions and adaptable for a spectrum of treatment stages and different recovery protocols in a comfortable, repeatable and intuitive manner in harmony with the immobilizer.

SUMMARY

According to embodiments of the disclosure, the positioning wedge is arranged to immobilize and position a limb among a plurality of predetermined angles. For example, in a shoulder-abduction pillow configuration, the positioning wedge is configured as a shelf for the arm to rest on to position the shoulder in abduction. Angular adjustability is achieved by adding or removing inserts or spacers that are removably attached to the main body of the positioning wedge. The positioning wedge may define a maximum angle selected as a common maximum angle and is arranged to step-up and step-down in angular configuration between the maximum angle and a minimum angle, such as 0 degrees.

In the configuration of a shoulder-abduction pillow, the positioning wedge is arranged to rest against the side of the truncal wall. The positioning wedge may attach to strapping or other components of a shoulder immobilizer and an arm apparatus to maintain it stable relative to the user, particularly as most body portions have complicated shapes such as curvatures that differ from person to person. The main body's first or second sides may be generally contoured to predetermined body portions to accommodate complicated shapes. For example, one side, such as the first side of the main body, may have a face contoured to rest against the truncal wall such that the positioning wedge is stable and does not rock when an arm is resting on it. The other or second side of the positioning wedge may be contoured to match the shape of an arm or a predesignated arm apparatus.

Separate or different identical wedge inserts can be placed between the first and second sides of the main body to increase an abduction angle in predetermined increments. Surfaces of the inserts and sides of the main body may be arranged to removably fasten to one another according to known fastener means, such as hook-and-loop, snaps, straps, etc. The wedge inserts may be formed as each representing increments of an angle for abduction, such as 15 degrees, or they may be differently sized, so the wedge may include a stack of different inserts to reach a predetermined abduction angle cumulatively.

While known positioning wedges include a single piece or multiple pieces, they are complicated and confusing to step-up or step-down to the desired angle. The single- or multiple-piece configurations require the positioning wedge to be physically cut to the required size or angle. However, due to limited resources at a clinic, there is no assurance that the modified positioning wedge corresponds accurately or consistently to a predetermined angle. Using separate, identifiable pieces simplifies the embodiments described so the overall brace or solution's usability and intuitiveness are improved. Additionally, existing positioning wedge devices create the problem of individual wedge segments being cumbersome to use, the wedge segments being incorrectly attached (leading to poor compliance), and individual wedge segments being easily misplaced. Existing positioning wedges further do not configure the wedge segments to be configured to a user's body contours or to have sufficient ventilation.

As the positioning wedge may be configured for a certain immobilizer and limb apparatus, it can be assured that the positioning wedge will comfortably position a user's limb relative to a body portion. The positioning wedge may be used separate from a certain immobilizer and/or apparatus and may be used with non-prescribed immobilizers and apparatuses.

These and other present disclosure features will become better understood regarding the following description, appended claims, and accompanying drawings.

Figure 1:
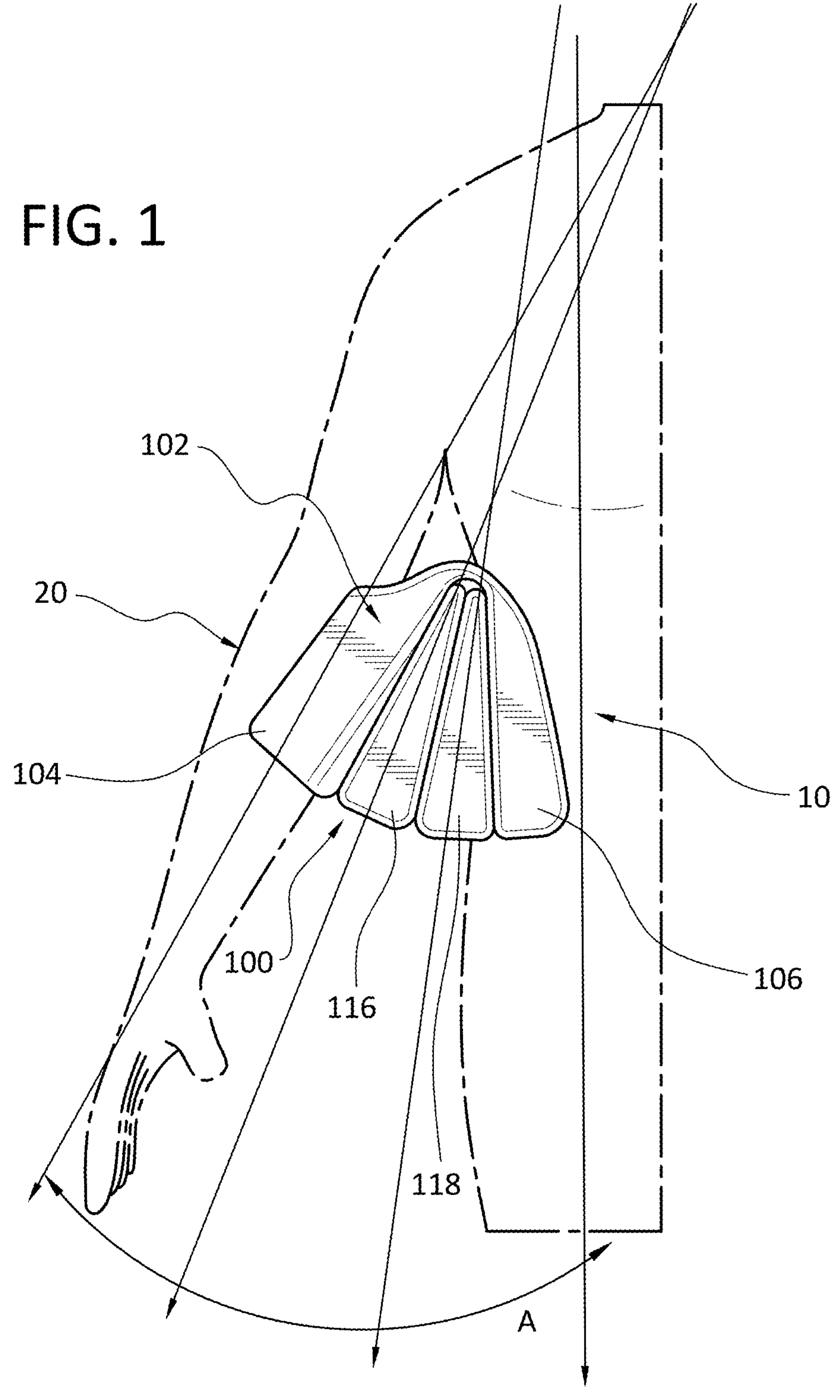
FIG. 1 is a schematic view of a positioning wedge exemplifying an ability to prop a limb among a plurality of angles relative to a body portion.

The drawing figures are not necessarily drawn to scale. Instead, they are drawn to provide a better understanding of the components and are not limited in scope, but to provide exemplary illustrations. The figures illustrate exemplary configurations of an orthopedic device, and in no way limit the structures or configurations of an orthopedic device and components according to the present disclosure.

DETAILED DESCRIPTION OF VARIOUS EMBODIMENTS

A. Introduction

Embodiments of a positioning wedge are provided for postoperative or post-injury suspension or propping of a limb relative to a body portion. In the following embodiments, the positioning wedge is described in the context of an abduction pillow for a shoulder such that the positioning wedge offloads the shoulder at a predetermined angle. The positioning wedge can be adapted to other indications, including a hip-abduction pillow. The positioning wedge is not necessarily solely adapted to suspend or prop a limb relative to a body portion. Still, it may be used against a non-body surface to suspend or prop a limb, such as a bed or other surface, in elevating a limb at a predetermined angle.

Although the embodiments of the disclosure are adapted for supporting and stabilizing anatomical portions of many users having various anatomical shapes and sizes, the embodiments of the disclosure may also be dimensioned to accommodate different types, shapes, and sizes of anatomical portions.

A better understanding of different embodiments of the disclosure may be had from the following description read with the accompanying drawings in which like reference characters refer to like elements. While the disclosure is susceptible to various modifications and alternative constructions, certain illustrative embodiments are in the drawings described below. It should be understood, however, there is no intention to limit the disclosure to the embodiments disclosed, but on the contrary, the intention covers all modifications, alternative constructions, combinations, and equivalents falling within the spirit and scope of the disclosure. Unless a term is defined in this disclosure to possess a described meaning, there is no intent to limit the meaning of such term, either expressly or indirectly, beyond its plain or ordinary meaning.

Reference characters are provided in the claims for explanatory purposes only and are not intended to limit the scope of the claims or restrict each claim limitation to the element in the drawings and identified by the reference character.

For ease of understanding the disclosed embodiments of a positioning wedge, the term superior is used to exemplify a position or range of positions above something or to approach such above something; an example would be towards or at a top of the positioning wedge is arranged in an upright manner as shown in FIG. 1. The term inferior is used to exemplify a position or range of positions below something or approaching such below something; an example would be towards or at a bottom if the positioning wedge is arranged in an upright manner, as shown in FIG. 1. While the wedge may be positioned sideways, upside down, or skewed for various uses, the terms superior and inferior are used in the context of the positioning wedge in an upright position, as illustrated.

The term longitudinal is used generally in the aforesaid upright manner, whereby longitudinal conveys relating to length, as in inferior to superior. The term lateral is used relative to longitudinal and conveys relating to the side or side to side, generally perpendicular to longitudinal, accounting for uneven and rounded possible surfaces.

The terms "rigid," "flexible," "compliant," and "resilient" may be used herein to distinguish characteristics of portions of certain features of the positioning wedge and associated devices and components. The term "rigid" should denote that an element is generally devoid of flexibility. Within the context of components that are "rigid," it should indicate that they do not lose their overall shape when force is applied. The term "flexible" should denote that features are capable of repeated bending. The features may be bent into retained shapes or the features do not retain a general shape but continuously deform when force is applied. As for the term "semi-rigid," this term is used to connote properties of components that provide support and are free-standing; however, such components may have flexibility or resiliency.

The term "compliant" is used to qualify such flexible features as generally conforming to the shape of another object when placed in contact therewith, via any suitable natural or applied forces, such as gravitational forces, or forces applied by external mechanisms, for example, strap mechanisms. The term "resilient" is used to qualify such flexible features as generally returning to an initial general shape without permanent deformation. The term "compressible" may qualify such structural features as being capable of being reduced in size or volume due to the exertion of force applied to the structural feature.

B. Embodiments of the Positioning Wedge

FIG. 1 exemplifies a positioning wedge 100 arranged as an interface between two anatomical or body portions 10, 20 of a human body to arrange the two anatomical portions 10, 20 at a predetermined angle A relative to one another. In this instance, the positioning wedge 100 abuts a torsal region or body, as a first anatomical portion, 10 of the user and props up the shoulder by positioning the arm or limb, as a second anatomical portion, 20 at an angle or among angles A relative to the torsal region 10. The positioning wedge 100 may be configured with a shoulder immobilizer and/or arm apparatus disclosed in the co-owned U.S. provisional application No. 62/925,057 filed on 23 Oct. 2019, having the title "Shoulder Immobilizer and Arm Apparatus."

The positioning wedge 100 includes a main body 102 with first and second sides 104, 106 arranged adjacent to the body 10, and the limb 20, respectively. At least one insert 116, 118 is arranged between the first and second sides 104, 106 at a predetermined angle associated with a shape of the at least one insert 116, 118. The positioning wedge 100 is modular in that it can be configured to position the first and second sides 104, 106 relative to one another among different angles.

In the depicted example, the first and second sides 104, 106 correspond to or define actual angular profiles 108, 110; however a profile itself may comprise the first and second sides 104, 106, if one of the discrete angular profiles 108, 110 is removed. Each angular profile 108, 110 itself may define the first and second sides 104, 106, and may correspond individually to an angular relationship among the first and second sides 104, 106, however in the illustrated example, the first and second sides 104, 106 correspond to discrete first and second angular profiles 108, 110, respectively. Preferably, the angular profiles 108, 110, and inserts 116, 118 define a wedge-like shape. The wedge-like shape may have a superior end having a different lateral width relative to an inferior end along a longitudinal line from the superior end S to the inferior end I. The wedge-like shape defines the angular profile in that it is arranged to articulate or arrange the first and second anatomical portions of a human body at an angle, and such angular profiles may be combined to construct other angular configurations aside from the angular profile of a given single wedge-like shape.

Referring to the illustrated embodiment of FIGS. 1-4, the at least one insert 116, 118 is detachable from the main body 102 to configure the positioning wedge 100 into different angles. In the example, the at least one insert 116, 118 comprises first and second inserts 116, 118 arranged to be inserted individually or collectively between the first and second sides 104, 106. The first insert 116 is arranged with a first insert profile 117 configured to arrange the first side 104 relative to the second side 106 at a first insert angle 126. The first insert profile 117 has a wedge-like shape, such as a triangular shape or other suitable shape corresponding to a predetermined angle along its longitudinal length, with an end portion 127 extending to a superior clearance 120 and a bridge portion 103 between the first and second sides 104, 106 at the predetermined angle 126.

The first and second inserts 116, 118 preferably interlock with one another and interlock with the first and second sides 104, 106. Likewise, when the first and second sides 104, 106 remain adjacent to one another without the first and second inserts 116, 118 located therebetween, the first and second sides 104, 106 preferably interlock with one another to prevent separating from one another. By usage of the term interlock, it means securing within one another in a fixed position, with means provided on each interlocking part to cooperate with one another to unite and prevent separating from one another, without generally intentionally doing so.

The first and second sides 104, 106 are continuously connected to one another by the bridge portion 103, meaning that the first and second sides 104, 106 are unitary with the bridge portion 103. The unitary construction allows for the first and second inserts 116, 118 to be removed from the wedge 100 as separate parts relative to the unitary construction of the first and second sides 104, 106, and the bridge portion 103.

Like the first insert 116, the second insert 118 is arranged with a second insert profile 119 configured to arrange the first side 104 relative to the second side 106 at a second insert angle 128. The second insert profile 119 has a wedge-like shape, such as a triangular shape, with an end portion 129 extending to the superior clearance 120 and the bridge portion 103 extending thereover between the first and second sides 104, 106 at a predetermined angle 126.

The first and second inserts 116, 118 are arranged to be positioned between the first and second sides 104, 106, and orient the first and second sides 104, 106 at an angle corresponding to a combined angle formed by the first and second inserts 116, 118. As illustrated, the first and second insert profiles 117, 119 are identical to one another, however, the first and second insert profiles 117, 119 may be different from one another, namely by their corresponding angles or shapes 126, 128. The positioning wedge 100 is not limited to just two inserts, but the bridge portion 103 may accommodate more or fewer than two inserts, with each insert corresponding to its own predetermined angle.

The provision of the bridge portion 103 between the first and second sides 104, 106 advantageously facilitates easy and intuitive insertion of the first and second inserts 116, 118 (or fewer or more inserts as desired) by providing a flexible and accommodating space in which the inserts 116, 118 can be received, but without requiring a cumbersome or confusing insertion/removal procedure. Nevertheless, the main body 102 provides an intuitive and highly repeatable process for consistently correct insertion and removal of the inserts 116, 118, thereby addressing the problem of existing devices that do not have a mechanism for consistently correct addition or removal of incremental wedge segments.

Additionally, by providing the first and second sides 104, 106 defining angular profiles 108, 110, the positioning wedge 100 defines body-conforming portions (such as the recesses 112, 114) that provide a comfortable and intuitive engagement with a user while also allowing the use of uniformly shaped, modular inserts for incrementally customizing the cumulative angle of abduction provided by the positioning wedge 100 as suitable based on an individual user's dimensions and rehabilitation progress.

The main body 102 may be formed continuously as a monolithic object from the same material, including the first and second sides 104, 106, and the bridge portion 103. The inserts 116, 118 may likewise be formed of the same material as the main body 102. Alternatively, the bridge portion 103 may be formed from a different material compared to the first and second sides 104, 106, and may be removably connected to them. For example, the first and second sides 104, 106 may be formed from foam or of a resilient and compressible material such as EVA (ethylene vinyl acetate), and the bridge portion 103 could be a textile connecting to the first and second sides 104, 106. The inserts 116, 118 could be formed from the same or different materials from the first and second sides 104, 106, and may be selected among materials for properties including compressibility, resiliency, flexibility, rigidity, or semi-rigidity.

The bridge portion 103 may be defined as a flexible segment of the material of the main body 102 or a separate material, extending between the first and second sides 104, 106 and arranged to permit the first and second sides 104, 106 to articulate relative to one another in setting the predetermined angle A of the positioning wedge 100. The bridge portion 103 may be a thinned segment and arranged to extend over none, one, or both of the first and second inserts 116, 118 depending on the predetermined angle A of the positioning wedge 100. For instance, the first and second sides 104, 106 of the positioning wedge 100 may be configured with a predetermined abduction angle if no inserts are provided, allowing a user or clinician to step-down treatment to a minimal level of abduction as needed, such as during the later stages of rehabilitation of a shoulder post-operation.

Figure 2:
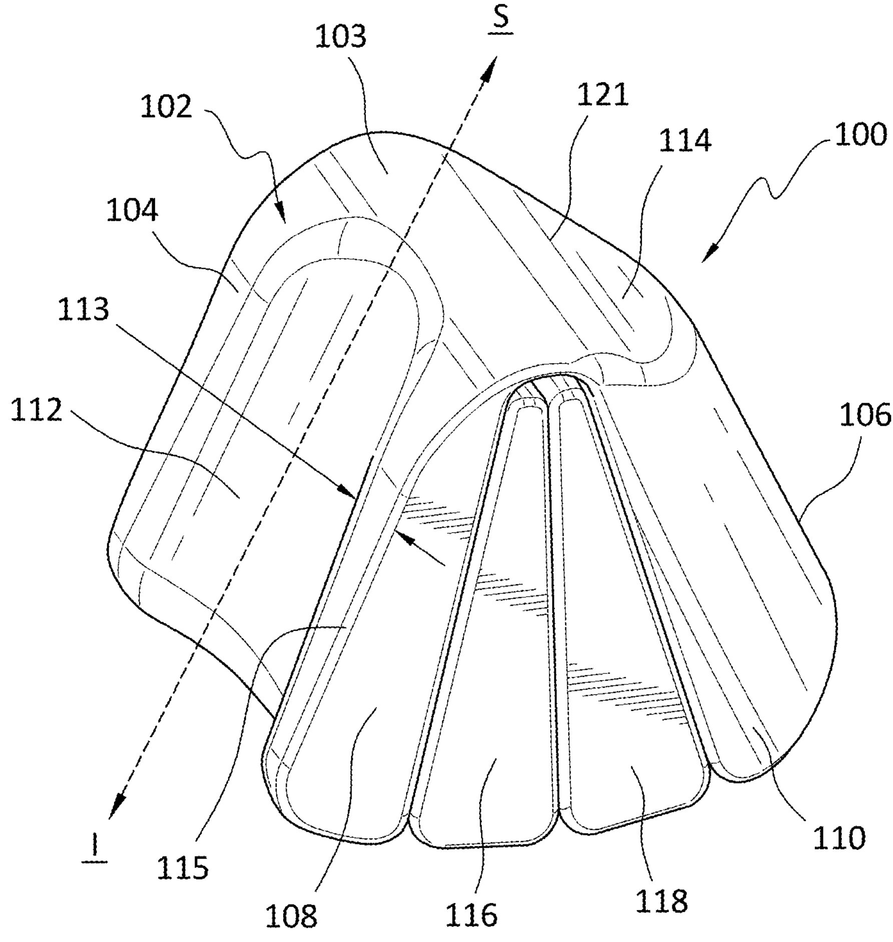
FIG. 2 is a perspective view of an embodiment of the positioning wedge of FIG. 1.
Figure 3:
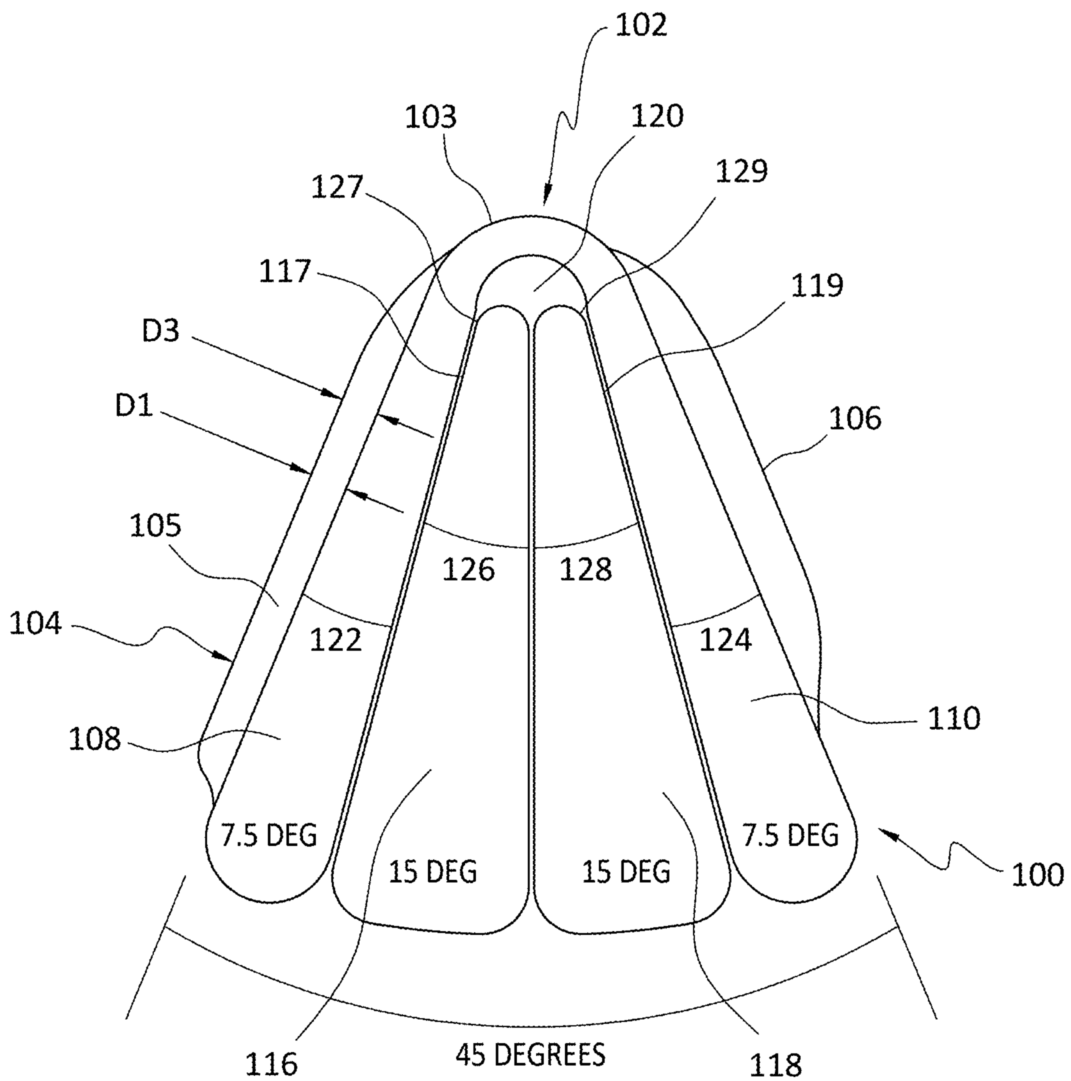
FIG. 3 is an elevational view of the positioning wedge of FIG. 1.

As illustrated in FIGS. 2 and 3, the first side 104 includes a first angular profile 108 defined as a cross-sectional portion of the main body 102, and the first angular profile 108 is arranged at an angle relative to the second side 106. While the first angular profile 108 may define a wedge-like or triangular shape articulating the first side 104 relative to the second side 106 at the bridge portion 103, the first angular profile 108 forms a predetermined angle 122 relative to the second side 106. A first protruding portion 105 may extend outwardly from the first angular profile 108 a first distance D1 from the first angular profile 108. A first recess 112 extends from the first side 104 a first depth at a third distance D3 at or short of the first distance D1.

The first recess 112 may be adapted to accommodate at least one of the first and second body portions 10, 20. The first recess 112 can extend a distance 113 away from an edge 115 or opposed edges 115 of the first angular profile 108 such that the first angular profile 108 generally maintains a consistent lateral profile without interruption from the first recess 112. The first recess 112 may generally extend superiorly S and inferiorly I of the main body 102. The first recess 112 tapers superiorly S relative to inferiorly I such that the first recess 112 flares toward opposed edges 115 of the first side 104 inferiorly I.

As with the first side 104, the second side 106 includes a second angular profile 110 defining a cross-sectional portion of the main body 102. The second angular profile 110 is arranged at an angle relative to the first side 106. The second angular profile 110 defines a wedge-like or triangular shape articulating the second side 106 relative to the first side 104 at the bridge portion 103. The second side 106 defines a second recess 114 adapted to accommodate at least one of the first and second body portions 10, 20.

As an example as to how the recesses 112, 114 along the first and second sides 104, 106 may be adapted to an intended purpose of the positioning wedge 100, the second recess 114 is shown as defining a profile 121 extending laterally at a superior portion of the second side 106. The second angular profile 110 may form a predetermined angle 124 relative to the second side 106. The second recess 114 is located at a superior portion of the second side 106 and directly extends from the bridge portion 103.

Figure 4:
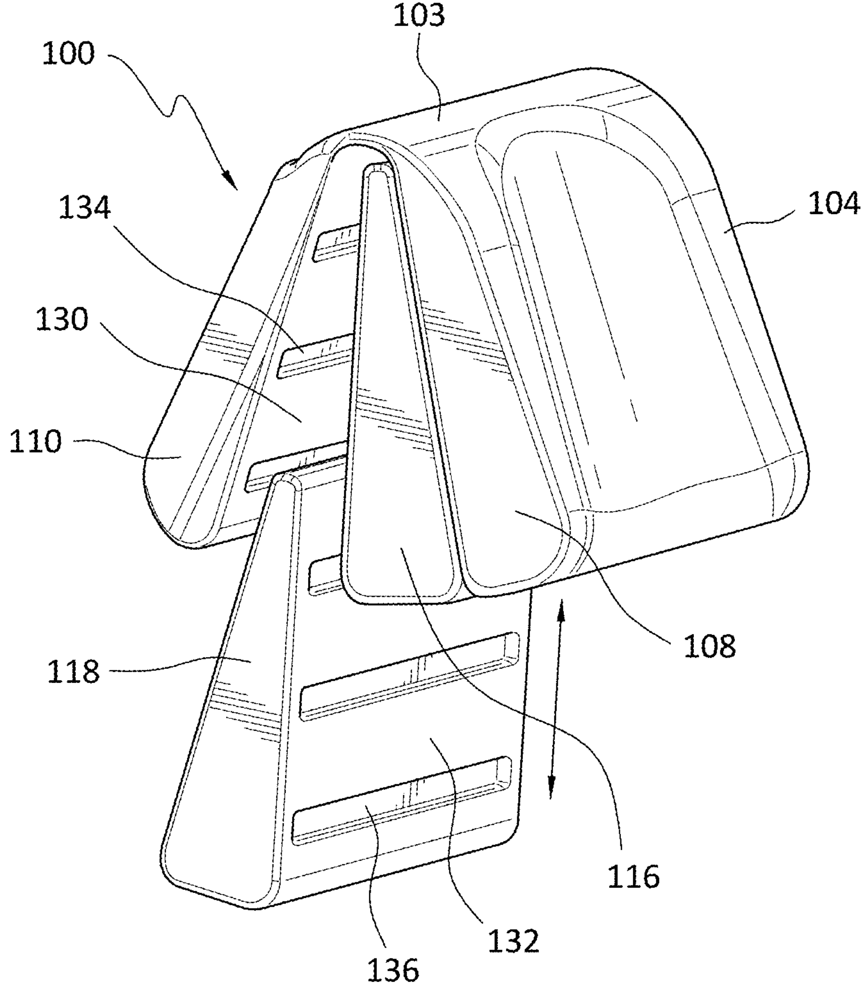
FIG. 4 is a schematic perspective view of the positioning wedge of FIG. 1 showing displacement of an insert relative to a main body.

FIG. 4 illustrates the first or second sides 104, 106, as defining an inner surface 130 arranged adjacent to an inner surface 132 of one of the first and second inserts 116, 118. The inner surface 130 of the first or second sides 104, 106 is arranged to removably secure the inner surface 132 of one of the first and second inserts 116, 118. Removal or addition of one of the first and second inserts 116, 118 correspondingly adjusts the angle A between the first and second sides 104, 106.

The inner surface 130 includes a fastener 134 engageable with a corresponding fastener 136 of the inner surface 132. The fasteners 134, 136 may be selected from among at least hook-and-loop material, snaps, interlocking portions of the inner surfaces 130, 132 such as a tongue-and-groove arrangement or a protrusion and corresponding recess, and other suitable means to secure one of the inserts 116, 118 to one of the sides 104, 106 during extended use of the positioning wedge 100. The inner surface 132 and corresponding fasteners 136 may be defined on either or both sides of the first and second inserts 116, 118, and can be arranged to cooperate with an adjacent insert or the opposite first and second sides 104, 106. Thus, when only a single insert 116, 118 is needed to provide a desired angle of abduction, the single insert 116, 118 is enabled to releasably secure to both the first and the second sides 104, 106 to ensure reliable functionality of the positioning wedge 100.

Figures 5, 6:
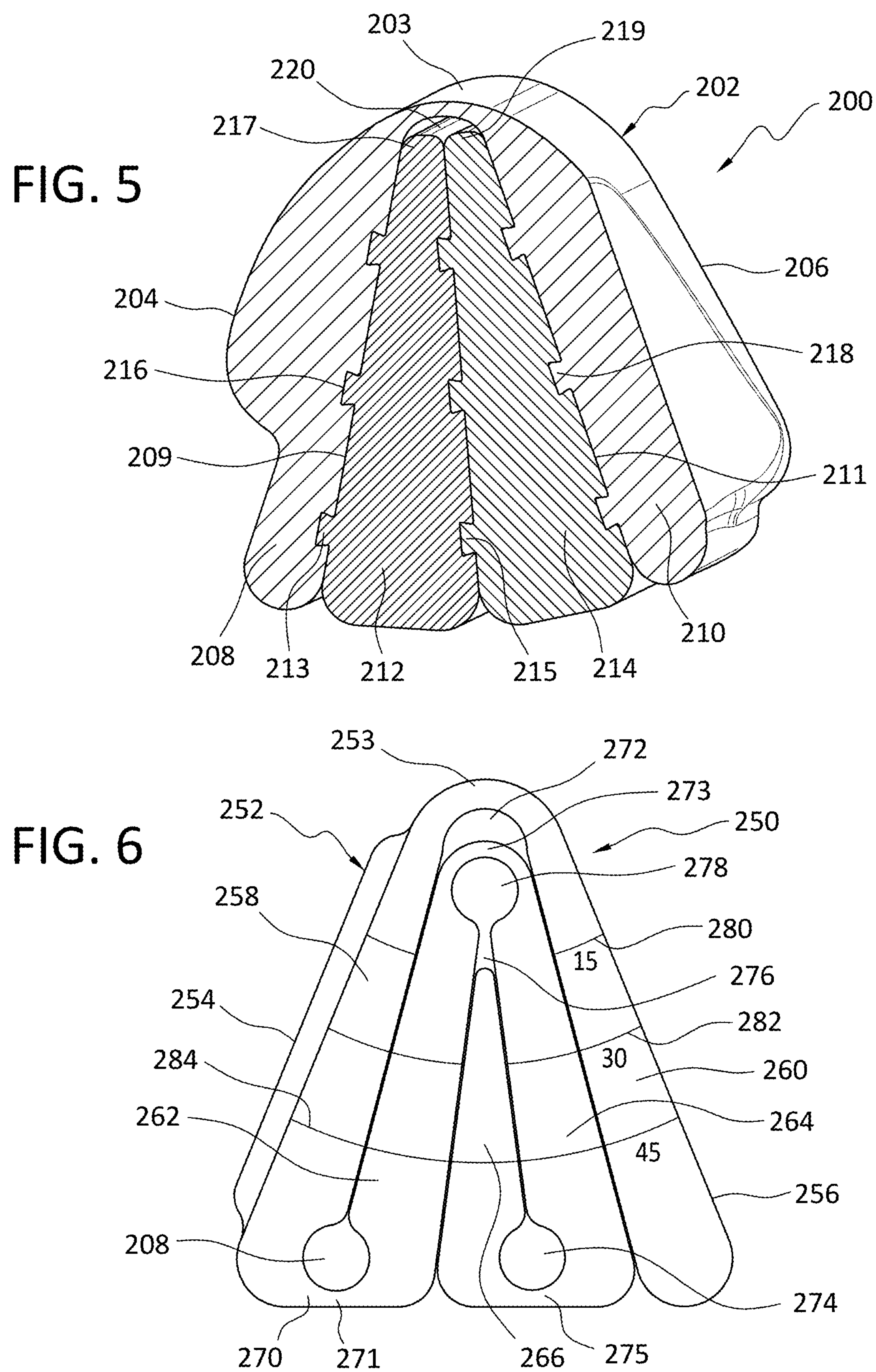
FIG. 5 is a cross-sectional view of another embodiment of a positioning wedge.
FIG. 6 is an elevational view of another embodiment of a positioning wedge.

FIG. 5 shows another embodiment of a positioning wedge 200 comprising a first side 204 connecting to a second side 206 by a bridge portion 203 located at a superior side of a main body 202. The first side 204 defines a first profile 208, and the second side 206 defines a second profile 210. The first and second sides 204, 206 have interlocking inner surface profiles 209, 211. In this embodiment, the interlocking inner surface profiles 209, 211 are defined by tongue 218 and groove 216 portions extending along with the first and second profiles 208, 210 of the first and second sides 204, 206, and corresponding to interlocking portions 213, 215 of first and second inserts 212, 214 so that any of the preceding portions can removably connect to one another.

A clearance 220 is preferably defined between the bridge portion 203 and superior end portions 217, 219 of the first and second inserts 212, 214. The clearance 220 is arranged to permit removal and addition of the first and second inserts 212, 214 between the first and second sides 204, 206.

FIG. 6 illustrates another embodiment of a positioning wedge 250. The main body 252 continuously forms the first and second sides 254, 256, and the bridge portion 253 is between the first and second sides 254, 256 about the superior end of the main body 252. The first profile 258 of the first side 254 continuously extends about the inferior end by a first inferior bridge portion 270 to a first insert 262. A first inferior opening 268 is bounded by the first inferior bridge portion 270 and the first profile 258. The first insert 262 extends continuously about a second superior bridge portion 273 nested inferiorly from the first bridge portion 253.

A first superior clearance 272 is located between the first and second superior bridge portions 253, 273. A second insert 264 extends from the second superior bridge portion 273 inferiorly and is located adjacent a second profile 260 defined by the second side 256. A second superior opening 278 is bounded by the second superior bridge portion 273 and the first and second inserts 262, 264. A second inferior bridge portion 275 extends continuously from the second insert 264 to a third insert 266, extending superiorly to below the second superior opening 278. A gap 276 is formed between the first and second inserts 262, 264, and superiorly of the third insert 266. A second inferior opening 274 is bounded by the second inferior bridge portion 275 and the second and third inserts 264, 266.

The positioning wedge 250 defines a plurality of tear-away zones 271 located between each of the inserts 262, 264, 266, and profiles 258, 260 to quickly facilitate sizing of the positioning wedge 250. The tear-away zones 271 may comprise thinned or perforated areas facilitating removal of inserts or profiles from one another. Alternatively, the tear-away zones 271 may comprise fasteners of any suitable variety such as hook-and-loop fasteners for releasably connecting and/or removing the inserts 262, 264, 266. While the depicted embodiment shows three inserts 262, 264, 266, it will be understood that fewer or more inserts may be provided as deemed suitable.

A first angular indicia 280 is located only on the first and second profiles 258, 260, representing an angle formed only by combining the first and second profiles 258, 260. A second angular indicia 282 is located only on the first and second profiles 258, 260, and the first and second inserts 262, 264, representing an angle formed only by combining the first and second profiles 258, 260 and the first and second inserts 262, 264. A third angular indicia 284 is located only on the first and second profiles 258, 260 and the first, second, and third inserts 262, 264, 266, representing an angle formed only by a combination of the first and second profiles 258, 260, and the first, second and third inserts 262, 264, 266, facilitating intuitive and effective sizing of the positioning wedge 250 by a clinician or a user.

FIGS. 7A-7D illustrate another embodiment of a positioning wedge 300. The main body 302 defines at least one lateral slot 316 extending through at least one of the first and second sides 304, 306, and/or between one of the first and second sides 304, 306, and at least one of the first and second inserts 308, 310. In the depicted embodiment, it is preferred that the at least one lateral slot 316 primarily or solely extends through one of the first or second sides 304, 306 and the corresponding profiles 305, 307 since it may be likely that the positioning wedge 300 will maintain both the first and second sides 304, 306 whether or not inserts are located therebetween. Multiple lateral slots may be provided in any of the profiles or inserts according to desired strapping configurations. At least one lateral slot 316 may facilitate attachment to components such as straps of a cooperating device as a shoulder immobilizer or sling.

The at least one lateral slot 316 is arranged for receiving at least one elongate strap 317 extending laterally through opposed lateral sides of the positioning wedge 300. The at least one lateral slot 316 is depicted as being defined through at least part of the second profile 307 of the second side 306 since the second side 306 may cooperate with a strapping assembly for a shoulder or at least maintains the positioning wedge 300 in a fixed location about a user's torso.

The main body 302 may define at least one longitudinal slot 318 extending through the first profile 305 of the first side 304. The at least one longitudinal slot 318 may extend arcuately through the first profile 305. The at least one longitudinal slot 318 may define at least two slots 319*a*, 319*b* opening along a face 309 of the first side 304, and extending through a thickness of the first side 304. The at least one longitudinal slot 318 may also serve as a conduit for ventilating the main body 302, with complimentary slots extending at least through the second side 304, and/or the inserts 308, 310. In alternative embodiments, the at least one longitudinal slot 318 may be arranged to cooperate with straps or components of other devices, such as an arm apparatus, as described in greater detail below. For instance, the at least one longitudinal slot 318 may be configured to receive a strap that extends around the body portion to form a circumferential engagement between the positioning wedge 300, the strap, and the body portion.

The at least one lateral slot 316 may define at least one hook portion 330*a*, 330*b* on opposed ends thereof. The at least one hook portion 330*a*, 330*b* generally extends along a height of the at least one slot 316. A clearance 328 is preferably defined between the at least one hook portion 330*a*, 330*b*.

Figure 7A:
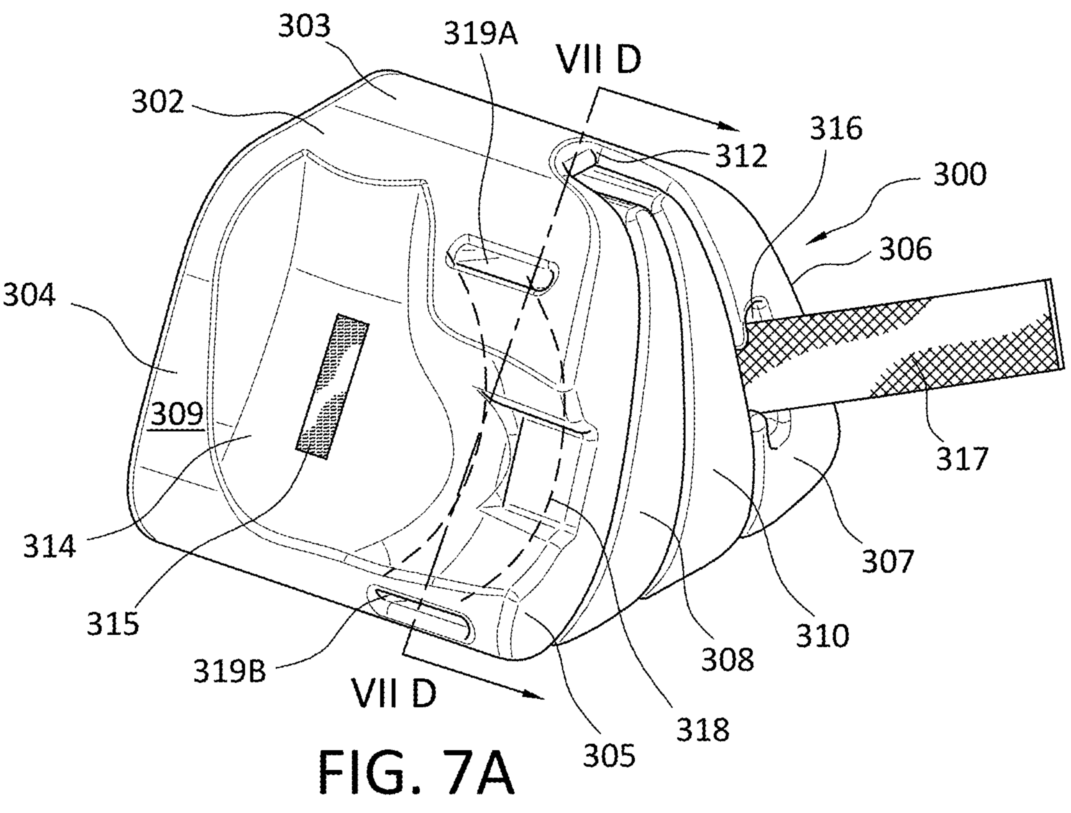
FIG. 7A is a perspective view of a first side of another embodiment of a positioning wedge.
Figure 7B:
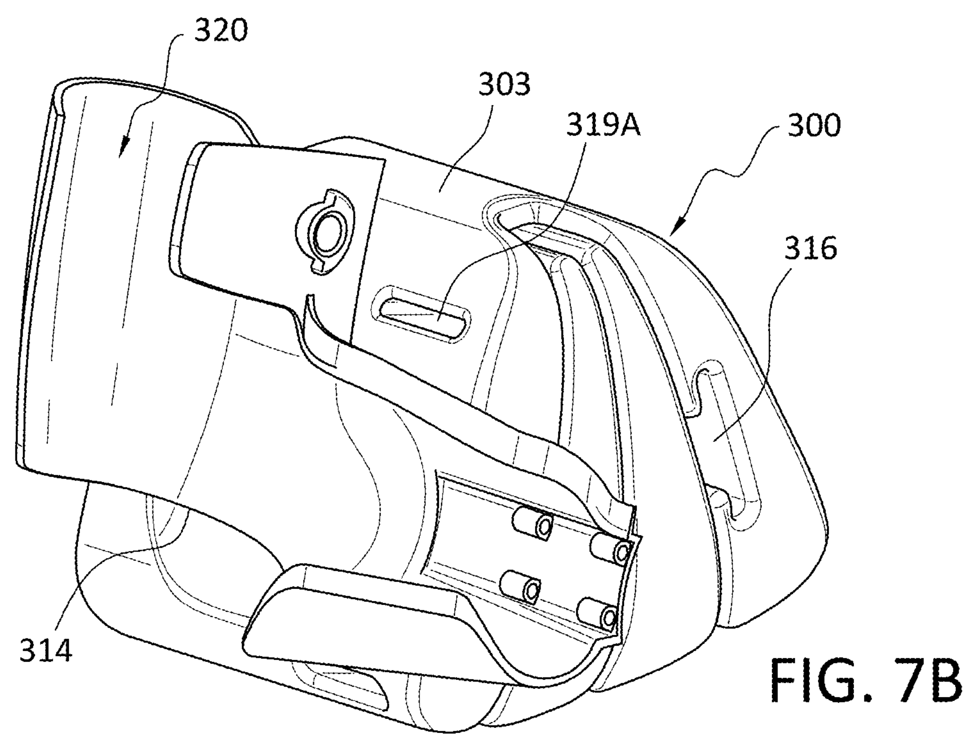
FIG. 7B is a perspective view of the positioning wedge of FIG. 7A with an arm apparatus attached thereto.
Figures 7C, 8A, 8B:
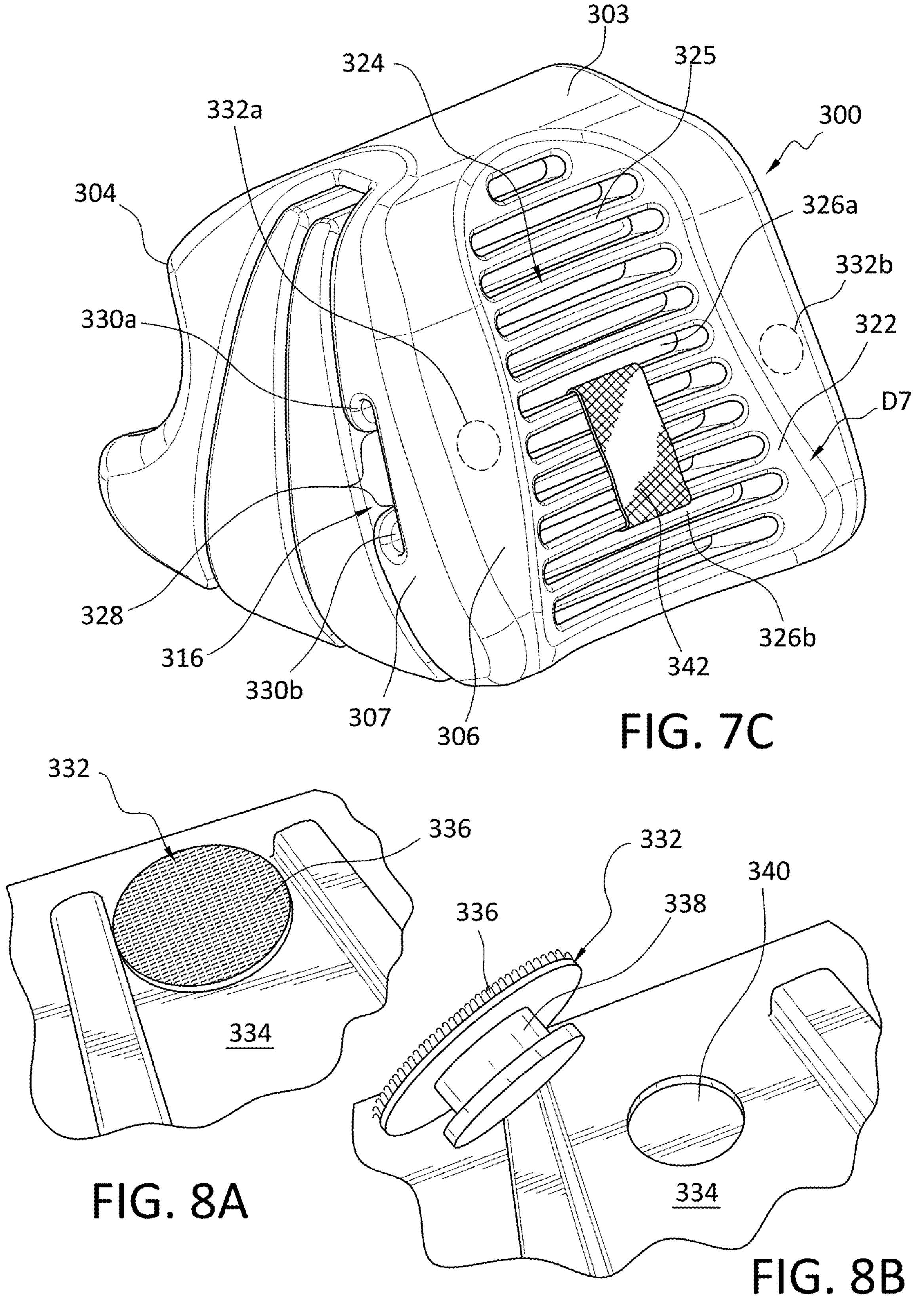
FIG. 7C is a perspective view of a second side of the positioning wedge of FIG. 7A.
FIG. 8A is a perspective view of an insert along a surface of the positioning wedge of FIG. 7A.
FIG. 8B is a schematic perspective of the insert of FIG. 8A separated from the positioning wedge.
Figure 7D:
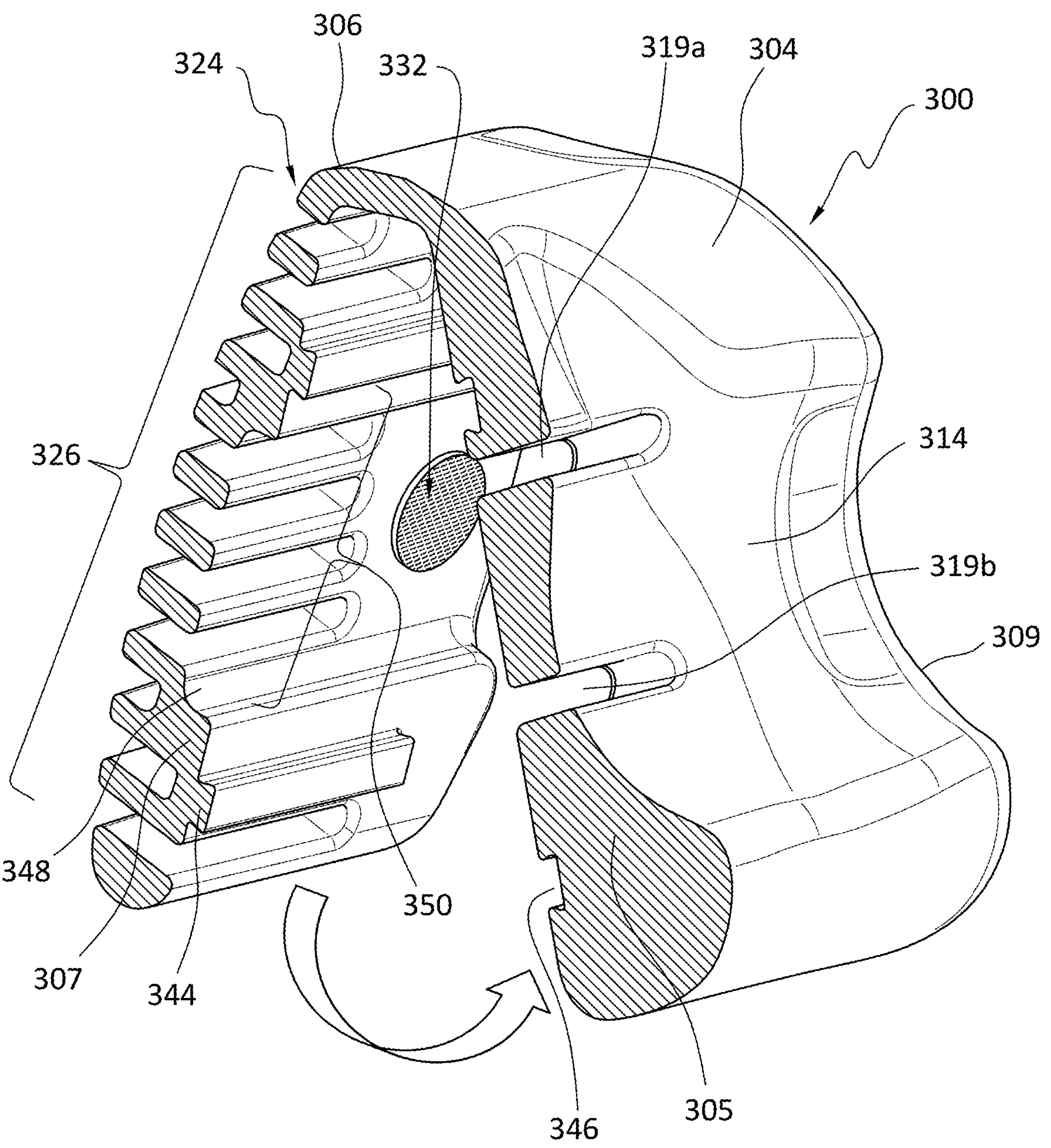
FIG. 7D is a cross-sectional view taken along line VII D-VII D in FIG. 7A.

FIGS. 7C and 7D show how a ventilation feature 324 on the second side 306 corresponds to the pair of slots 318*a*, 318*b* on the first side 304. The ventilation feature 324 and the pair of slots 318*a*, 318*b* extend through an entirety of the first and second profiles 305, 307. The ventilation feature 324 may extend over a substantial entirety of a longitudinal length of the second side 306, and includes a plurality of ventilation slots 326 formed through a thickness of the profile 307 of the second side 306 and defined by a corresponding plurality of transverse ribs 325. The first side 304 be arranged with a similar ventilation feature as the second side. Among the plurality of ventilation slots 326, at least two ventilation slots 326*a*, 326*b* may be arranged to receive a strap 342 configured for being wrapped thereabout.

The ventilation feature 324 may define a relief 322 on an outside surface of the second side 306 corresponding to a shape of the truncal region of the body, thereby minimizing the overall profile of the positioning wedge 300 and providing improved fit and comfort. For instance, the ventilation feature 324 including the ventilation slots 326 defined by the transverse ribs 325 may be recessed a distance D7 from the outermost surface of the second side 306.

The second profile 307 may have thickness variations 348 to bolster a thickness of the profile 307 and have a corresponding tongue 344 arranged to interlock with a groove 346 defined by an inner lateral surface of the first profile 305. When interlocked, the tongue and groove 344, 346 engage sufficiently to avoid the first and second sides 304, 306 from separating, however, due to a preferred resiliency of a material forming the positioning wedge 300, a user or clinician can separate the first side 304 from the second side 306 by squeezing or otherwise manipulating the tongue and groove connection 344, 346 to separate the first and second sides 304, 306. The ventilation feature 324 may also define a relief 350 on an inner surface of the second side, with a number of the ventilation slots 326 extending through the thickness of the profile 307 being spaced a distance laterally apart from an innermost section of the inner surface, i.e., at the tongue 344. In this manner, the ventilation feature 324 defines sufficient space for air and heat transfer away from the user's body portion to occur through the spaces defined by the plurality of ventilation slots 326.

The first side 304 defines a contoured recess 314 formed along the face 309 and is configured and dimensioned to receive an arm apparatus 320, for example, an arm apparatus as described in greater detail in the aforementioned co-owned U.S. provisional application No. 62/925,057. The contoured recess 314 is form-fitted to an exact configuration of a side of the arm apparatus 320. The contoured recess 314 can be adapted or formed for other devices or a general profile of an arm to hold an arm better close thereto. A fastener 315 may be located within the contoured recess 314 for securing to a corresponding fastener on the arm apparatus 320. The arm apparatus 320 may have any suitable configuration or material (including compliant slings, rigid arm braces, and otherwise), and the contoured recess 314 likewise may define any suitable configuration to cooperate therewith. A material of the positioning wedge main body 302 proximate the contoured recess 314 may be formed from a material of increased softness, breathability, or compliance relative to a remainder of the main body 302 to softly cushion a user's arm, for instance, if no corresponding arm apparatus 320 is provided.

The contoured recess 314 is not limited to the shape described herein but may be adapted to different sizes and shapes, depending on the indication for which the wedge is used. An advantage of a contoured recess, as opposed to a generic recess, is that it enables the wedge to cradle an anatomical portion and/or apparatus secured to the anatomical portion of a user. This same desirability of the contoured recess, or any other body-conforming portions, allow the wedge to cradle and support anatomical portions, such as those that are opposing one another.

The main body 302 may include a clearance 312 formed along a superior bridge 303 connecting the first and second sides 304, 306, and providing access to superior ends of the first and second inserts 308, 310.

Referring to FIGS. 8A and 8B, an inner surface 334 of at least one of the first and second sides 304, 306 defines at least one opening 340 arranged for receiving a fastener insert 332. The fastener insert 332 includes a fastener element 336 and a mount 338 adapted to secure to the at least one of the first and second sides 304, 306 by the at least one opening 340. First and second fastener inserts 332*a*, 332*b* are defined, for example on an inner surface 334 of the second side 306.

While the fastener inserts are shown as hook and loop fasteners, alternative fasteners may be used to secure parts and sides of the wedge together. For example, corresponding "mushroom" type snaps or fasteners may be provided on certain sides and sections, for insertion into corresponding an inner surface profile, such as an opening, enabling the mushroom type snaps to couple with the side or insert carrying the openings. Using such snap fasteners, whether a mushroom type or other known type of interlocking fastener, enables a clinician to snap in and maintain the wedge together, including parts and sides, together firmly. A balance between harder snaps for possible better retention, and softer snaps for possible better comfort, can be considered when selecting the fasteners.

Figure 7E:
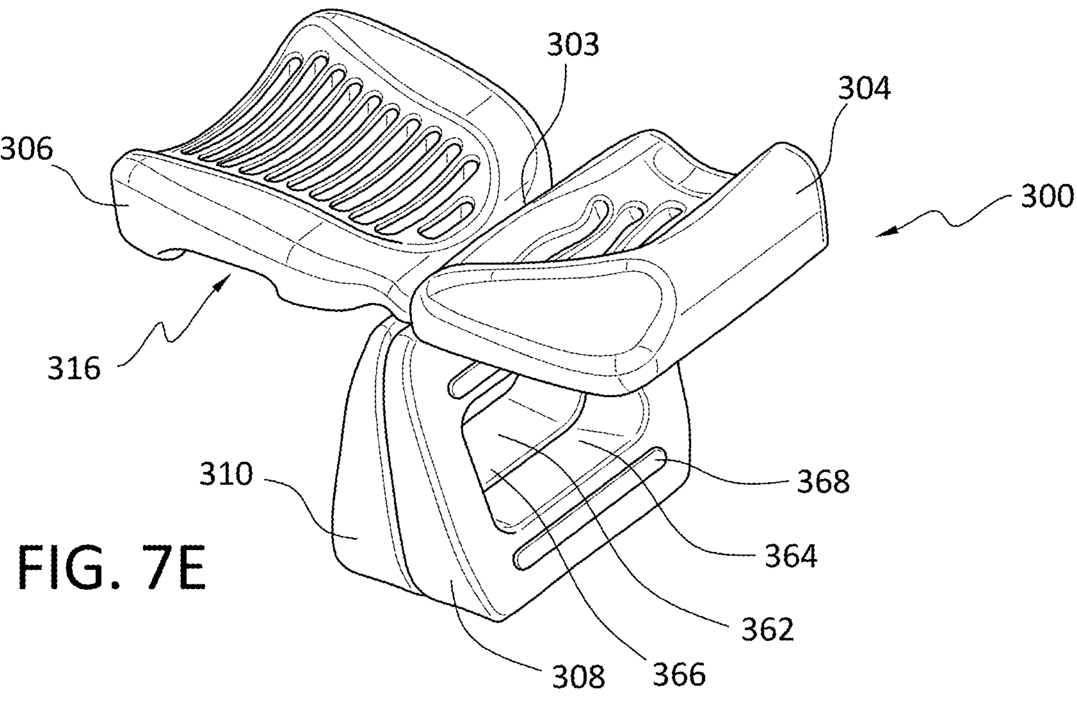
FIG. 7E is a perspective view of a first side of a variation of the positioning wedge of FIG. 7A.
Figure 7F:
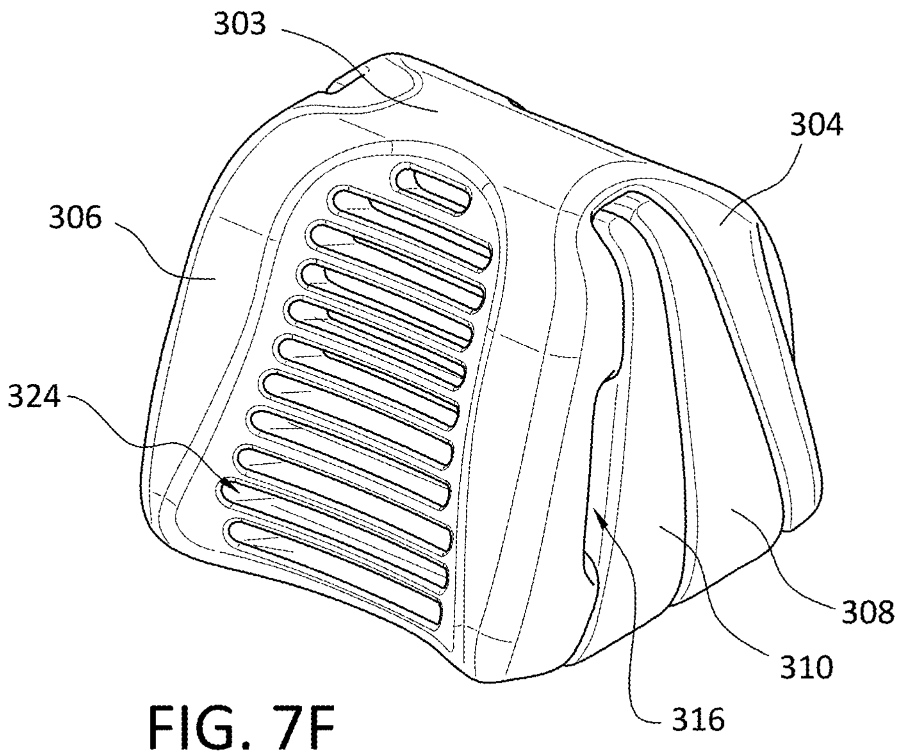
FIG. 7F is a perspective view of a second side of the positioning wedge according to the variation in FIG. 7E.

In a variation of the positioning wedge 300 with first and second sides 304, 306 rotated superiorly to expose first and second inserts 308, 310 as shown in FIGS. 7E-7F, an additional ventilation feature is provided in the first and second inserts 308, 310. The first and second inserts 308, 310 may define first and second ventilation spaces 362, 364, respectively, configured to facilitate transfer of air and heat between and away from the body portions 10, 20 supported and positioned by the positioning wedge 300.

The first and second ventilation spaces 362, 364 may comprise a substantial entirety or a majority of an interior portion of the first and second inserts 308, 310, such that remaining first and second outer bevels 366, 368, respectively, remain and space the first and second inserts 308, 310 by a desired degree from the first and second sides 304, 306.

The provision of the first and second ventilation spaces 362, 364 advantageously improves ventilation and heat transfer (as air and heat are enabled to transfer much more freely through the resulting open space within the positioning wedge 300), reduces the weight of the positioning wedge 300, and avoids sacrificing the needed structural strength of the overall positioning wedge 300 due to the provision of the bevels 366, 368.

It will be appreciated that the depicted embodiment is merely exemplary, and the ventilation spaces 362, 364 may take any suitable structure or form. For example, the first and second inserts 308, 310 may alternatively comprise a material having greater porosity than the main body 302. The first and second inserts 308, 310 may define a ventilation feature 324 with ventilated slots 326 defined by a plurality of ribs. The ventilated slots 326 defined by the ventilation feature of the first and second inserts 308, 310 may align with each other and with the ventilated slots 326*a*, 326*b* of the main body 302, or may be staggered relative to the ventilated slots of adjacent structures, for example to reduce an overall profile of the positioning wedge 300, to provide additional structural support, or otherwise.

The ventilation feature is not limited to elongate slots, as shown, but may include round openings or any other shape suitable for offering ventilation and reducing bulk of the wedge. Any of the slots or shapes of openings may be repurposed for insertion of straps or belts of any type described herein.

By providing a positioning wedge according to the disclosure's embodiments, the problem of existing foam blocks and other positioning devices being imprecise, cumbersome to use, poorly ventilated, and poorly configured for attachment to complementary and cooperating devices such as immobilizers and limb apparatuses is addressed. The positioning wedge of the disclosed embodiments advantageously provides an improved positioning wedge that can be configured for use between any suitable body portions and provides a customizable, intuitive, and effective solution for providing the desired level of support and unloading of a particular body portion.

While the disclosure discusses embodiments for the shoulder, positioning wedge embodiments of the disclosure may be used with other limbs, joints, and anatomical portions, including the torso, shoulder, elbow, wrist/hand, hip, knee, and foot/ankle, and including between any suitable body portion and any suitable structure, such as to provide abduction or unloading of a shoulder or hip relative to a bed, a chair, a couch, or any other surface.

Not necessarily all such objects or advantages may be achieved under any embodiment of the disclosure. Those skilled in the art will recognize that the disclosure may be embodied or carried out to achieve or optimize one advantage or group of advantages as taught without achieving other objects or advantages as taught or suggested.

The skilled artisan will recognize the interchangeability of various components from different embodiments described. Besides the variations described, other known equivalents for each feature can be mixed and matched by one of ordinary skill in this art to construct a positioning wedge under principles of the present disclosure. Therefore, the embodiments described may be adapted to systems for securing, supporting, or comforting limbs or another anatomical portion.

Although a positioning wedge has been disclosed in certain preferred embodiments and examples, it will be understood by those skilled in the art that the present disclosure extends beyond the disclosed embodiments to other alternative embodiments and/or uses of the disclosure obvious modifications and equivalents. It is intended that the scope of the present disclosure disclosed should not be limited by the disclosed embodiments described above but should be determined only by a fair reading of the claims that follow.

The invention claimed is:

1. A positioning wedge adapted to interface between two anatomical portions of a human body to arrange said two anatomical portions at a predetermined angle or position relative to one another, comprising:

a main body having first and second parts connected to another by a bridge portion, the first and second parts defining a predetermined angular first and second profiles, respectively;

at least one insert arranged between the first and second parts to position the first and second parts relative to one another at a predetermined angle associated with a shape of the at least one insert, the at least one insert being separable from and attachable to the main body and the bridge portion extending over an end portion of the at least one insert;

wherein the first part defines at least one lateral slot extending laterally through opposed lateral sides of the positioning wedge.

2. The positioning wedge of claim 1, wherein the second part defines a contoured recess formed along a face thereof.

3. The positioning wedge of claim 2, wherein a fastener is provided within the contoured recess.

4. The positioning wedge of claim 2, wherein the second part defines at least one longitudinal slot extending through the second profile.

5. The positioning wedge of claim 4, wherein the at least one longitudinal slot extends arcuately through the second profile, and first and second slots are formed along a face of the second part, and extending through a thickness of the second part; wherein the first and second slots are located above and below the contoured recess, respectively.

6. The positioning wedge of claim 4, wherein the at least one longitudinal slot extends arcuately through the second profile, and at least two slots are formed along a face of the second part, and extending through a thickness of the second part.

7. The positioning wedge of claim 1, wherein the second part defines at least one longitudinal slot extending through the second profile.

8. The positioning wedge of claim 1, wherein at least one fastener is located along an inner surface of the first part defining the least one lateral slot.

9. The positioning wedge of claim 8, wherein the inner surface defining the at least one lateral slot of the first part forms at least one opening arranged for receiving the at least one fastener.

10. The positioning wedge of claim 1, wherein the first part defines a ventilation feature.

11. The positioning wedge of claim 10, wherein the ventilation feature is defined by openings formed through a thickness of the profile.

12. The positioning wedge of claim 11, wherein the ventilation feature includes a plurality of transverse ribs between each of the openings.

13. The positioning wedge of claim 10, wherein an exterior surface of the first part forms a surface relief.

14. The positioning wedge of claim 13, wherein the surface relief is configured in shape to receive to a truncal region of a human body.

15. The positioning wedge of claim 1, wherein the main body is formed from a resilient and compressible material.

16. The positioning wedge of claim 1, wherein the at least one insert forms a ventilation space extending through a thickness thereof.

17. The positioning wedge of claim 1, wherein the first and second parts increase in thickness from the bridge, wherein a greatest thickness of the first and second parts is at an opposite end thereof relative to the bridge.

* * * * *